US012654027B2

(12) United States Patent
Lin et al.

(10) Patent No.: US 12,654,027 B2
(45) Date of Patent: Jun. 16, 2026

(54) MYOPIA-PREVENTING HIGH INTENSITY ILLUMINATION APPARATUS FOR ILLUMINATING EYEBALLS AND SURROUNDING TISSUES VIA LIGHT THAT PENETRATING PERIORBITAL SKIN, SUBCUTANEOUS TISSUE, THEN PASS THROUGH CORNEA, IRIS, UVEA, SCLERA AND CHOROID

(71) Applicants: Chwen-Yih Lin, New Taipei City (TW); Yu-Hao Lin, New Taipei City (TW)

(72) Inventors: Chwen-Yih Lin, New Taipei City (TW); Yu-Hao Lin, New Taipei City (TW)

( * ) Notice: Subject to any disclaimer, the term of this patent is extended or adjusted under 35 U.S.C. 154(b) by 819 days.

(21) Appl. No.: 17/903,046

(22) Filed: Sep. 6, 2022

(65) Prior Publication Data

US 2022/0409924 A1      Dec. 29, 2022

Related U.S. Application Data

(63) Continuation-in-part of application No. 17/014,201, filed on Sep. 8, 2020, now abandoned.

(51) Int. Cl.
*A61N 5/06* (2006.01)

(52) U.S. Cl.
CPC .... *A61N 5/0622* (2013.01); *A61N 2005/0648* (2013.01); *A61N 2005/0662* (2013.01)

(58) Field of Classification Search
CPC .......... A61N 5/0622; A61N 2005/0648; A61N 2005/0662; A61N 5/0613; A61N 5/06–2005/073
See application file for complete search history.

(56) References Cited

U.S. PATENT DOCUMENTS

| | | | | | |
|---|---|---|---|---|---|
| 11,974,374 | B2 * | 4/2024 | Linder | .................. | H05B 47/11 |
| 2021/0329764 | A1 * | 10/2021 | Linder | .................. | G02C 11/10 |

* cited by examiner

*Primary Examiner* — Jonathan T Kuo
(74) *Attorney, Agent, or Firm* — Guice Patents PLLC

(57) ABSTRACT

The present invention provides a myopia-preventing illumination apparatus for illuminating eyeballs and surrounding tissues via light that penetrating periorbital skin, subcutaneous tissue, then pass through peripheral cornea, iris, peripheral lens, uvea, sclera and choroid, retinal pigment epithelium, comprising multiple light source, two units for pupil detector and a CPU controller electrically connects to the light source, wherein the light source provide high intensity light pass through extra pupillary pathway to illuminate eyeball and surrounding tissue so as to provide benefit effect for preventing myopia progression.

11 Claims, 7 Drawing Sheets

(I)

(II)

MYOPIA-PREVENTING HIGH INTENSITY ILLUMINATION APPARATUS FOR ILLUMINATING EYEBALLS AND SURROUNDING TISSUES VIA LIGHT THAT PENETRATING PERIORBITAL SKIN, SUBCUTANEOUS TISSUE, THEN PASS THROUGH CORNEA, IRIS, UVEA, SCLERA AND CHOROID

This application is a Continuation-in-part Application of U.S. patent application Ser. No. 17/014,201, filed on Sep. 8, 2020.

BACKGROUND OF THE INVENTION

Field of the Invention

The present invention relates to a myopia-preventing high intensity illumination apparatus for illuminating eyeballs and surrounding tissue by extra pupillary pathway via light that penetrating periorbital skin, subcutaneous tissue, pass through peripheral cornea, iris, peripheral lens, uvea, sclera, choroid, retinal piment epithelium, specifically a device and method through extra pupillary pathway to apply high intensity illumination to eyeball and periorbital region.

Background

Many studies found that high intensity light illumination for eyeball has great effects on public health, studies (1-9) found that children stay enough outdoor time can prevent myopia progression, animal study found that ambient light by LED illumination of 40000 lux can stop the chicken myopia progression, while another study of Oyama et al., (2019, Cell Reports 28, 1471-1484) (10) found that full spectrum ambient light by 10000 lux can protect animal from heart injury, besides, they illuminated full spectrum light of same intensity on healthy human for half hour a day for one week, they found the aggregate (triglyceride) of glucose metabolism lowered, then the authors suggest that heart diseased human to receive high intensity light therapy for one week before heart surgery in order to increase the heart muscle protection, but the study admitted that they cannot standardized the pathway and angle of the main light incident to the eyeball.

So many studies suggest that high intensity light illumination is important in prevention of myopia, heart disease and diabetes mellitus (DM). But most of all did not understand that due to the convergence effect of lens in eyeball, most incoming light through pupil will convergent and focus on fovea of macula, hence in practical study we found that human cannot stand for staring at light which is pass directly through pupil of intensity more than 1500-2000 lux for a long time. In study of Oyama et al., the experiment animal is mouse that reared in a box of limited space, since mouse is a nocturnal animal, it will avoid high intensity light and turn their head and find an angle to low down the light illuminated into their eyeball, many light will fall on their eyelids, only light that partially blocked by eyelids, the reared mouses can stand the light of intensity of 10000 lux shine on their eye region, this is also true when they studied on light of 10000 lux illuminated on healthy human, they found and admitted that their illumination method and light angle is not standardized, in fact healthy human will turn their head to avoid the high intensity light to directly shine into their pupil otherwise their macula will be damaged.

The outdoor sunlight can easily reach the intensity of 40000-120000 lux and in excess to 200000 lux, in review of photograph taking from sunny seashore we found most people turn their head away from gazing sun, turn their head to the shadow side, or look downward or sideward, to avoid the sun from direct shine into their pupil, if in need of looking at sunny side, they will partially close the eyelids and turn a little downward to prevent sunlight from directly shine into the pupil. This is also true for animal raised in high ambient light, it will avoid ambient light from directly shine through their pupil, especially for nocturnal animal like mouse. Light of intensity greater than 2000 lux will shine on skin of eyelids and pass-through skin or through extra pupillary pathway to illuminate eyeball.

The light pass through extra pupillary pathway will penetrate the periorbital skin, subcutaneous tissue, pass through peripheral cornea then pass through iris, peripheral lens, into vitreous, then on peripheral retina, or pass backwardly through conjunctiva then pass through sclera, then pass through ciliary body or uvea tract or choroid or pass through retinal pigment epithelium, then backwardly into peripheral retina, the majority of light not convergent by lens to focus on macula, while it fall mostly on the peripheral retina, which is the main retinal area effective in myopia control found by many studies.

Most people thought that light therapy to eyeball need to shine the light directly on front of eyeball, but the light entering the front face of eyeball will convergent and concentrated by lens, the intensity of light will be greatly increased, hence the front incoming light will be limited by light intensity of 1500-2000 lux, or it will burn and damage the retina, especially the macula.

Studying the structure of eyeball, light shine directly on front of pupil or ocular region, the light will inevitably pass-through pupil, it will convergent and focus by lens of eyeball on a small area of retina. Due to the convergence and concentration effect by lens, the light intensity of incident light will be limited to 1500-2000 lux, and the light fall only on a small area of retina, In other words, light therapy to ocular region, if the pupillary pathway not blocked, the light intensity will be limited to lower than 1500-2000 lux, and the light shine only on small area of retina, This is the drawback of every prior art for myopia control.

While the high intensity light pass through extra-pupillary pathway to shine on eyeball play an important role on control of human health.

In view of this, we found that high intensity light in outdoor activity, it affects eyeball and periocular tissue through extra pupillary pathway, in a diffuse and relatively backward shine on eyeball. Only light intensity lower than 2000 lux will pass through pupillary pathway which is important for image detect and focus and convergent only on small area of retina, especially on macula. The high intensity light of more than 2000 lux shine eyeball by extra pupillary pathway, it pass through skin, subcutaneous tissue, peripheral cornea, iris, peripheral lens, ciliary body or sclera, uvea tract, choroid, retinal pigment epithelium, partially backwardly into retina, especially on most retina. The peripheral retina construct most of the eyeball retina, it is the major area of retina which controls the heath of human.

Modern people live in a style of lacking high intensity light illumination. In Asia, school children lack of outdoor activity due to competition for credit, many studies found that increase outdoor activity time will lowdown the myopia progression. While the outdoor time need to influence the myopia progression is 2-3 hour a day, most student cannot afford it. Hence the myopia rate in asia is top of the world, and due to modern lifestyle of high near work, high cell phone time, high indoor TV time, WHO estimated the world myopia rate of 2050 will approach 50%. This is a great health issue.

Heart disease and diabetes meliasis is also increased in recent years. Many studies found that high light outdoor illumination has positive effect on decrease the rate of those diseases.

Even healthy people in normal work is lacking enough outdoor illumination, they live in a modern house with standard light intensity of 500 lux. Get up early in morning, then drive car to office, and work in artificial lighting workspace of 500 lux illumination, then when complete day time work, they drive back home, still live into home of 500 lux illumination. The intensity of normal outdoor day light is 40000-200000 lux, far above the lighting standard of 500 lux in classroom and modern workspace and living house. Lacking enough outdoor time of high outdoor illumination is a public health problem for modern human.

Beside school children and indoor worker, many diseased people admitted to hospital bed ward, cannot afford outdoor activity, they lack high intensity light illumination, their heart and glucose metabolism will be greatly hampered. They are also in need of high intensity illumination to improve their health.

Many studies (1-9) suggested high intensity light is effective for myopia control; animal study succeed in control of form deprivation myopia by high intensity light therapy. Ambient light was suggested for the factor for myopia control. Intrinsically photosensitive retinal ganglion cell (ipRGC) was proposed as ambient light detector, melanopsin was its photopigment, but the ipRGC also receive signal of rod and cone cell, In the retina, ipRGCs provide excitatory drive to dopaminergic amacrine cells and ipRGCs are coupled to GABAergic amacrine cells via gap junctions.

Several subtypes of ipRGC have been identified (11). Besides that, dopamine also was suggested as a factor chemical for myopia control, and since the ipRGC connect with so many cells existing in the human orbital system, so many cells, so many chemicals involved, each factor play a role in the control of myopia and human physiology, some prior art with photo therapy focus only on a few photopigments, may neglect important factor in between, besides, many prior arts with photo therapy of front approach, light will inevitably mostly enter pupil zone and shine on small region of retina and by effect of lens the light intensity will be limited to only 1500-2000 lux, their effect on myopia control will be very limited. While the new method of our invention with light through extra pupillary pathway, the light will shine on most retina, which the most ipRGC distributed, in this pathway, ipRGC will be shine more completely and the high light intensity will more fit with our true world and the light intensity of successful myopia control experiments in prior studies, in other words, extra pupillary pathway of light therapy play an important role.

In study of outdoor activity we found that due to avoidance of direct shine by sunlight, people will wear hat, take umbrella, walk into shadow of tree or shelter, or in case of no shelter to avoid direct sun shine into pupil, they will turn backward or sideward or downward of their head, or closing their eyelids or wear sunglasses, we found that only about one twentieth of outdoor time that the sun light shine directly on eye region.

So if we can provide an illumination apparatus with safe and high intensity and high efficient full spectrum light to shine on eye region, only 10 to 15 minutes will equivalent to 3 to 5 hours of sun effect in outdoor activity, it will greatly help for health of those who cannot afford receiving enough outdoor time.

So, it is the goal of our invention to provide a method and device for high intensity and highly efficient light illumination of eyeball and periorbital region, through extra pupillary pathway which the light illumination intensity can approach 40000 lux to 200000 lux for the improvement of human health.

Description of the Prior Art

Myopia is a worldwide problem, especially in Asia. Myopia tends to develop in childhood and progress in severity until adulthood. Myopia associates with many disadvantages such as inconvenient in work, cost for glasses or contact lenses as well as increasing eye diseases relate to myopia. Hence, the prevention of progression of myopia is a great health issue.

PRIOR ARTS

One invention CN101858573A depicts a high illuminance classroom lamp, to apply high illuminance light to the students for preventing myopia. Another invention EP3141282A1 depicts a device for treating, preventing, or reducing myopia, or the risk thereof, using a display in front of student to apply various lights (illuminance of 0.6 to 1000 lux) to stimulate eyes. Another invention US20170072218A depicts a method and apparatus for reducing or preventing myopia, applying a display for temporal stimulate the viewer to prevent myopia. Another invention EP2155041A1 depicts a method for determination of optical adjustments to retard myopia progression, providing an anti-myopia lens to retard myopia progression. Another invention U.S. Pat. No. 9,709,826B2 depicts a method of applying ocular lens with filtered bands of wavelength to prevent myopia progression. Another invention WO2015152818A1 depicts a device to prevent the condition or disease associated with lack of outdoor time, applying a wearable device to monitor the outdoor time of children to prevent myopia progression. Another invention CN107707763A depicts a myopia prevention and control wearable device and myopia prevention and control system and method, applying a wearable device for monitor the reading illuminance and reading distance to prevent the progression of myopia. Another invention CN106289395A depicts a student myopia prevention and control wearable device, applying a wearable device with ambient light sensor and temperature sensor and laser distance sensor to monitor the student's reading pattern to prevent the myopia progression.

In US20190328577 A1 Luttrell et al, they depict a device with precision optics to apply pulsed light through pupil into retina for light therapy, their design is different from our invention in that in our invention the light is pass through mostly extra pupillary pathway while in their method the light can only pass-through pupil.

In U.S. Ser. No. 10/052,497 B2 Deisseroth et al, one of their embodiments depicts fiber optic in front of eye to stimulate ocular region, in their design the light will inevitably pass-through pupil, the light power can only limited to very low level.

In WO 2016040534 A1 Tedford et al, they depict an eye glasses with light that pass from ear piece to front piece then reflect to eyeball region, their design the light is inevitably pass through pupil, the light intensity will be limited to very low level.

In JP 2018509983 A Samek et al, one of their embodiments depicts VR or AR with extension light therapy device to apply light in front of eyeball region, their light route will pass through pupil, hence their design cannot apply high intensity light therapy to eyeball.

In US 2018/0345034 A1, they depict light therapy with selected wave length applying an eye glass frame or face mask in front of eye region, to illuminate the front eyeball, their light will inevitably pass greatly by pupil into eyeball, despite they declare they use light with intensity averaged to 9000 lux, in practical use their design will damage the retina, due to they do not block the light from entering the pupil pathway, their design is different from our invention that in our design the light is totally pass-through extra pupillary pathway, and the light intensity can be elevated to a more high level.

In US 2018/0280718 A1 Tsubota et al, they depict an eyeglasses or hat or wearable device with light of 350-400 nm to shine on front of eyeball, in their design the light shine through pupil, and the harmful UV light, collectively limited their light intensity.

The effectiveness of the prior arts is not confirmed, yet the myopia rate all over the world is still high, hence, there is high demand for an effective myopia preventing method or device.

SUMMARY OF THE INVENTION

The primary object of the present invention is to construct a myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, then into retina and vitreous to induce the subtle biochemical reaction which preventing the progression of myopia. Besides that, the light is directed by well-known pupil detection method by aid of computer and camera to prevent high intensity light pass-through pupil into eyeball to injury retina. In this design the light intensity can be elevated to as high as 10000 lux to 200000 lux and keep eyeball safely unharmed. And by dynamic avoidance of highly intensive light pass through pupil, the illumination efficiency is greatly increased. The spectrum of light in our invention is preferred to be full spectrum of day light to mimic outdoor activity but due to many theories about what spectrum is effective in myopia prevention is not well proved, the spectrum used will not be limit in our unique extra pupillary lighting method.

DETAILED DESCRIPTION OF THE PREFERRED EMBODIMENTS

Figure 1:
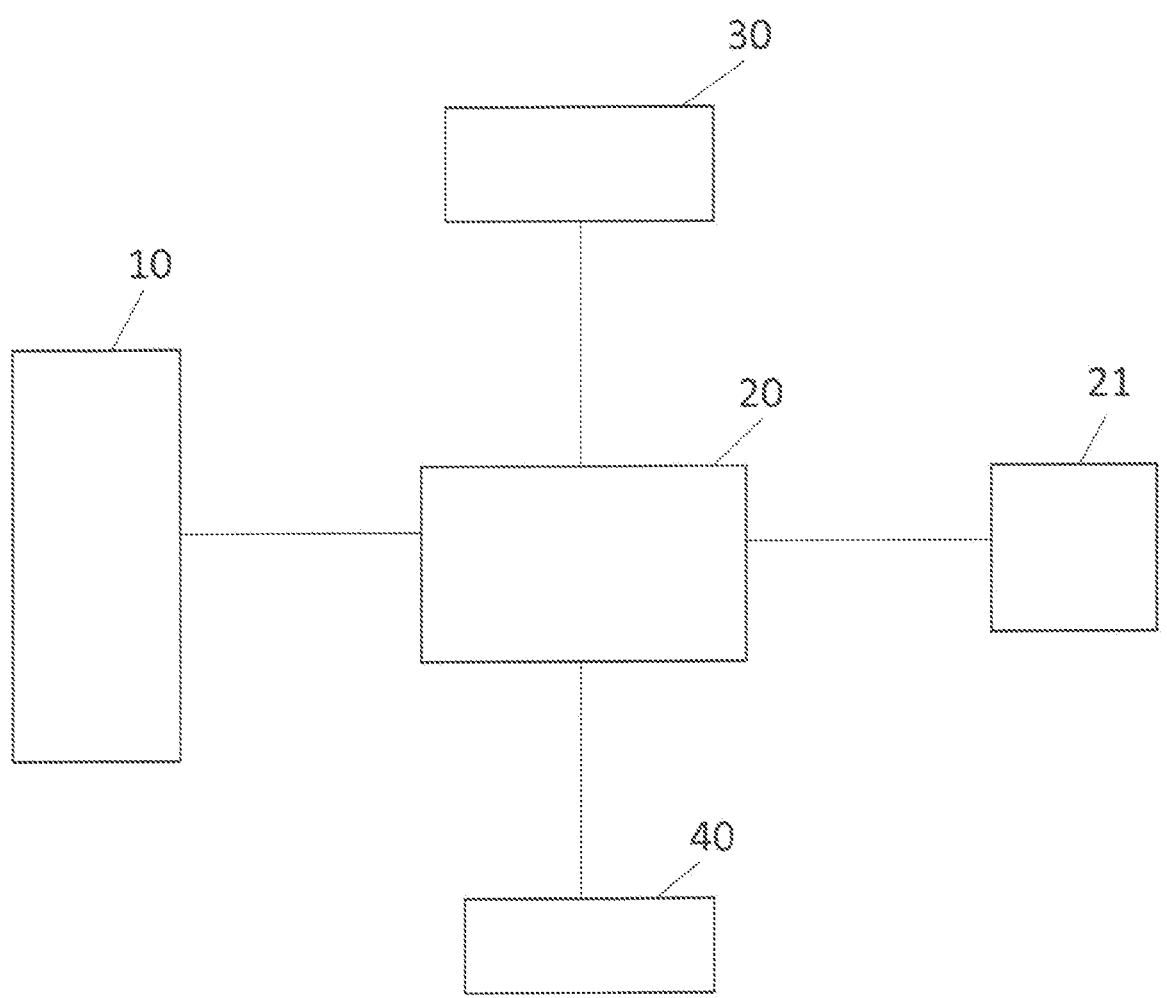
FIG. 1 is the system block diagram of the present invention.

Referring to the FIG. 1, the present invention comprising multiple light source 10, two units for pupil detector 40 and a CPU controller 20 and a battery 21 pack for system power supply; wherein the light source 10 comprises various spectra, and the spectra and composition thereof can be adjusted according to the requirement; the light source 10 can be one type of light source or a composition made up of various light sources, and the illumination level provided by the light source 10 is adjustable and can be adjusted based on different time periods, and the illumination level is greater than 0.5 LUX or program adjusted; the illumination timing of the light source 10 can be continuous, intermittent, or adjusted as preset program, the illumination period and brightness level can be modified and adjusted on the basis of a clock 30, and the illumination time each day can be adjusted according to a requirement with respect to different myopic person. The preferred illumination light intensity is averaged but not limited to 40000-120000 lux to mimic sunny daylight. The preferred light spectrum is full spectrum of sunny daylight but not limited to it.

Figure 2:
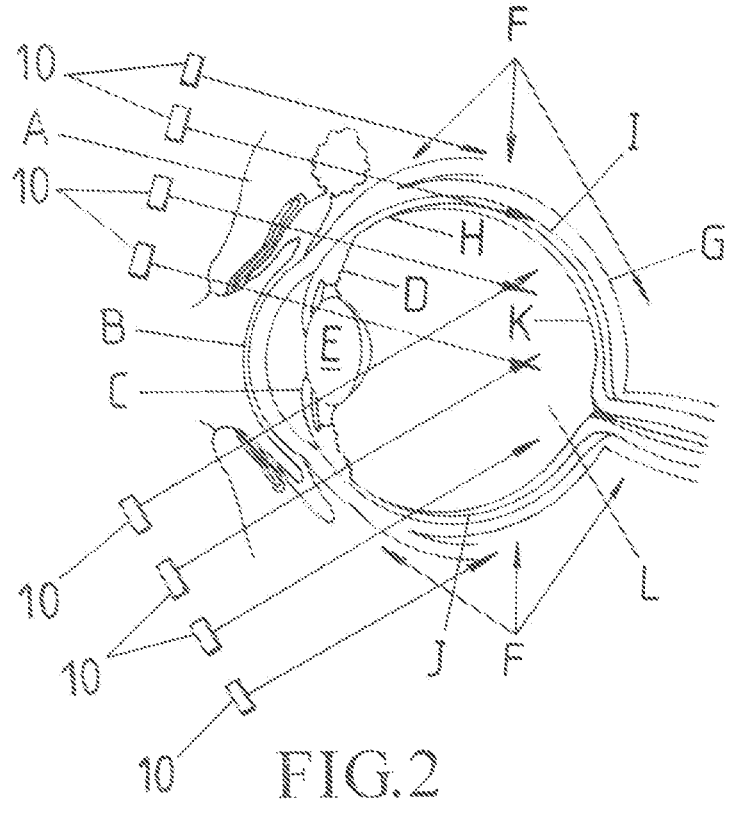
FIG. 2 is the schematic diagram illustrating the main route of light of the present invention.
Figure 2A:
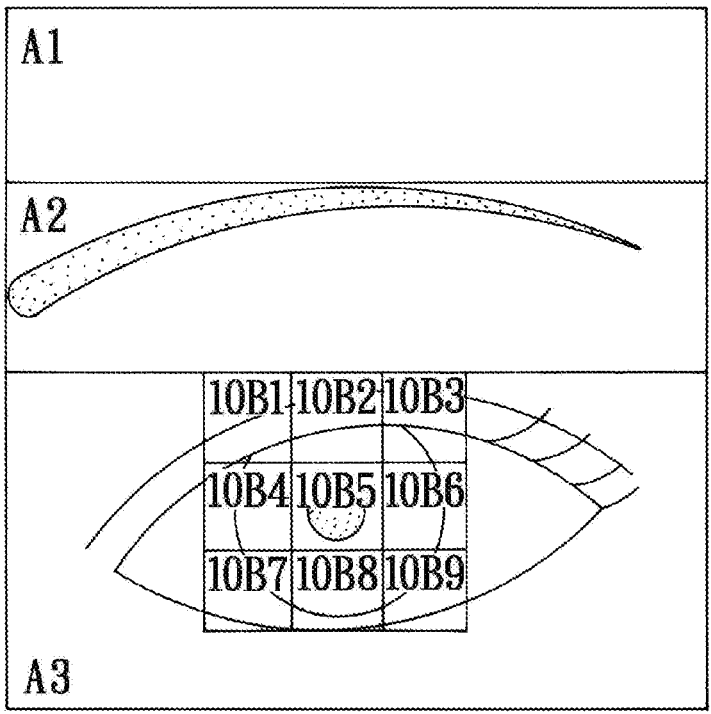
FIG. 2A is the schematic diagram of each different illumination area.
Figure 2B:
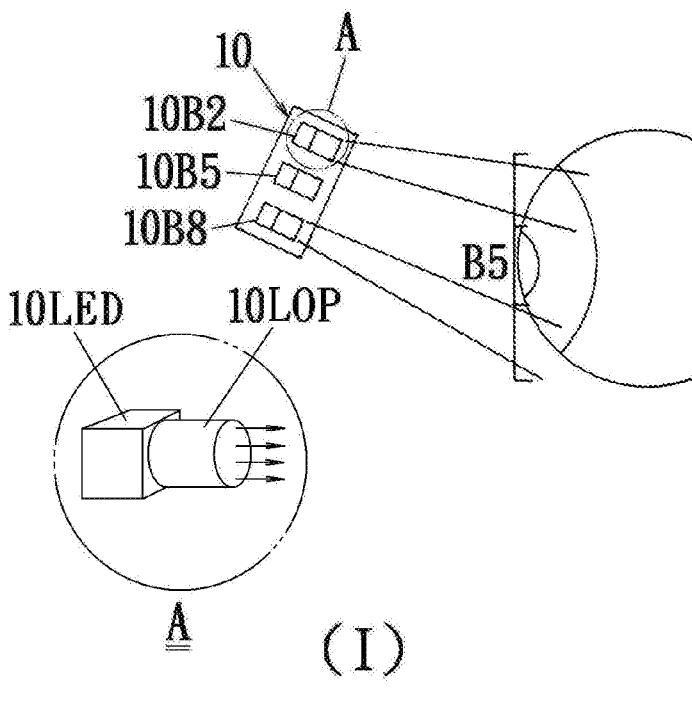
FIG. 2B is the schematic diagram illustrating illumination of each fine individual light element for cornea region, and its options of arrangement.
Figure 2B:
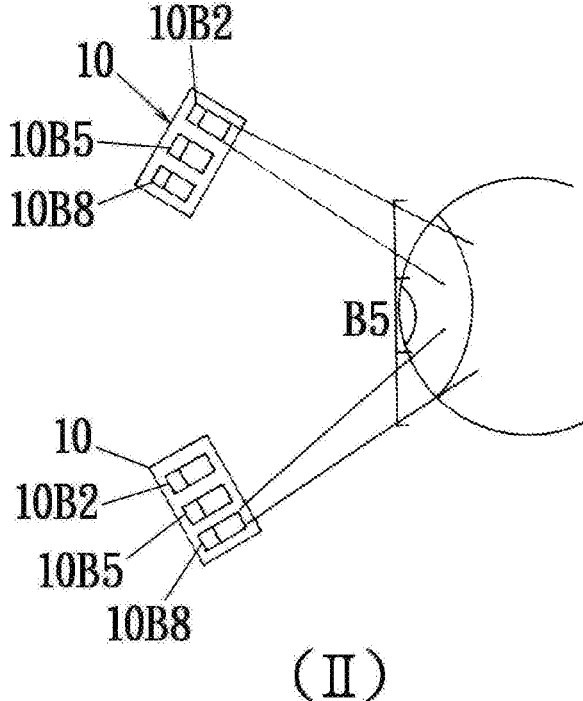
Figure 2C:
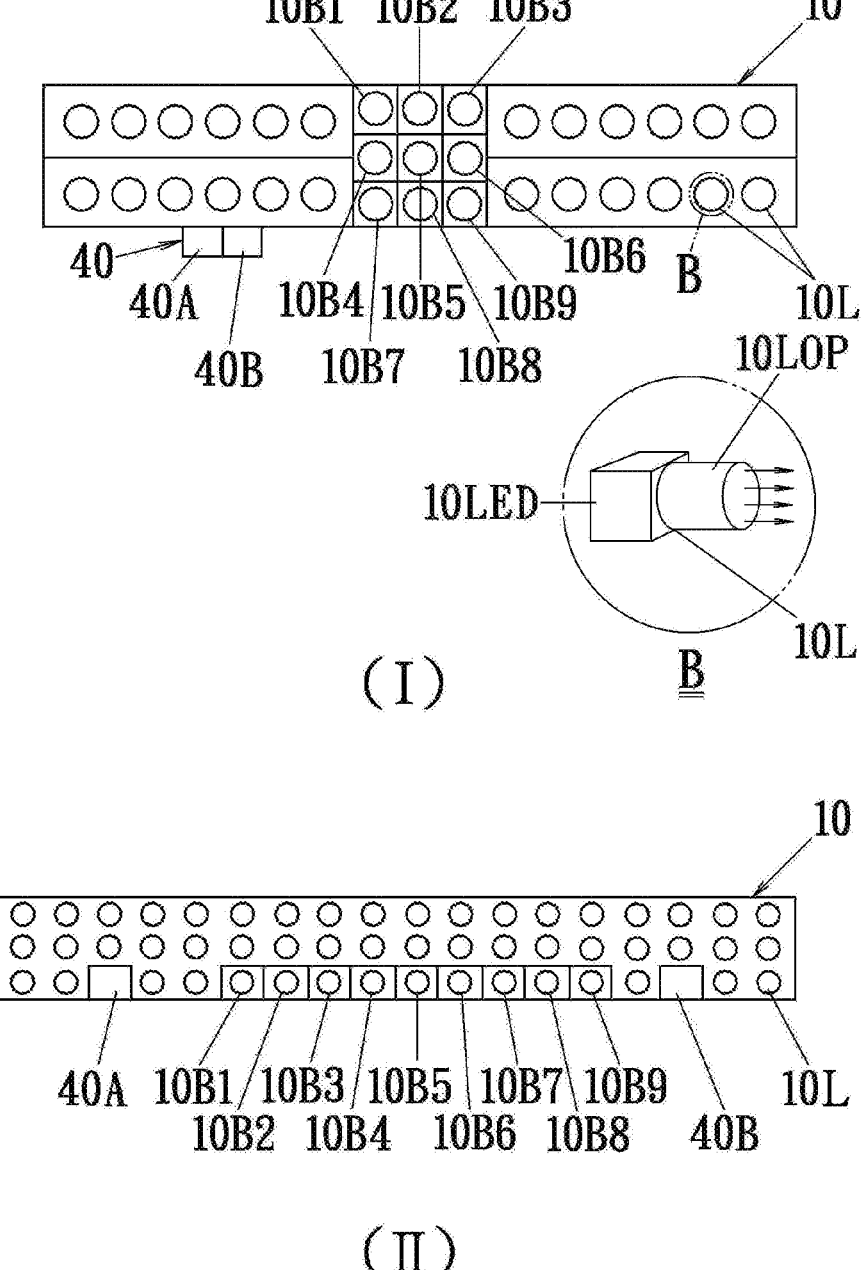
FIG. 2C is the schematic diagram of options of light source arrangement, and the arrangement of pupil detector.

The light source 10 composed of arrays of customized directed light element (FIG. 2C(I)(II)) which individually direct light to different eyeball front region to cover the most eyeball front area includes eyelids.

The light element of light source 10 illuminate the eyeball from an inclined angle compared to visual axis. The individual light element can be individually controlled by CPU controller 20 through fine circuit to turn on or off.

The pupil detection 40 is well-known knowledge, we use it in our invention. The pupil detector 40 composed of an infra-red LED light source 40A and a camera 40B, (FIG. 2C(I)(II)) the pupil detector 40 will send photo of pupil position to CPU controller 20, the CPU controller 20 will calculate whether the pupil position overlap with the illuminating position of fine individual light element (10B1-10B9) (FIG. 2A,2B) of light source 10. In case that any fine individual light element (10B1-10B9) illuminate area overlap with pupil region, (FIG. 2A,2B) the CPU controller 20 will calculate it out and shut that fine individual light element off in real time, in order to prevent high intensity light to enter into pupil, In this invention, the light illumination intensity can be as high as 10000 lux to 200000 lux, so keep the light illuminate eyeball only by extra pupillary pathway is necessary for preventing macular and retinal injury.

The CPU controller 20 is a CPU and is electrically connected to the light source 10 and the clock 30, wherein the controller 20 is electrically connected to a battery 21, and the battery 21 supplies power required for the light source 10, the CPU controller 20 and the clock 30. The battery 21 has option of connect to line power supply in case of recharge or high power consumption.

Referring to FIG. 2, at least one light source 10 of the present invention is projected to and illuminated on skin surrounding eyes, penetrates subcutaneous tissue A, then pass through peripheral cornea B, iris C, peripheral lens E, ciliary body D, or penetrates peripheral tissue F of eyeball, sclera G, uvea H, choroid I, retinal pigment epithelium J, backwardly enters into vitreous L and retina K, so as to prevent myopia from further progress by inducing microscopic biochemical reactions, which is still not well clarified, despite many theory were proposed, but only high intensive illumination to eyeball succeed in preventing myopia, but every prior art select the front approach without protection of pupil entrance, their practical light intensity will be limited to below 2000 lux, and lost its effect. In our invention, we choose the extra pupillary pathway, this is very similar to the outdoor activity of animal and human, that the high intensity outdoor light only passes into eyeball by extra pupillary route.

The embodiments of the present invention has many unlimited design, and can have various types of architectures:

FIG. 2A, designate the different illuminated area near eye, light illuminating A1, A2, A3, the intensity can be elevated to 10000 lux to 120000 or in excess to 200000 lux, as real outdoor sunlight, while the fine individual light element (10B1-10B9) of light source 10 illuminate to B1 to B9 area respectively will be controlled by the pupil detector 40, by comparison of overlapping photo calculated by CPU controller 20, any fine individual light element (10B1-10B9) of light source 10 illuminating area within B1 to B9 overlapping with pupil zone, its individual electric power will be shut off by CPU controller 20, its electric power will be on again in time of the overlapping is not continued, the calculating frequency is continuous, in a real time fashion. The areas of B1-B9 are 5 mm square each, comprises of a total of 15 mm square which cover the average human cornea size of 11-12 mm in diameter.

FIG. 2B, designates the light pathways of the light source 10, the light source 10 comprises of array of fine individual light element (10B1-10B9) which has customized optic to guide its light direction and were controlled by CPU controller 20, 10LED is the light producing element which produce light, 10LOP is the customized optic for guiding the light direction, the individual light element can stake in horizontal version or vertical version, the light source 10 can be arranged to illuminates from upper position or from upper and lower position. The light source 10 illuminate to A1, A2, A3 will not need to be regulated by pupil detector 40, since those area is far away from pupil zone.

FIG. 2C designates the options of light source arrangement, since the LED technology improved in recent years, we can select LED of high power and small, we can select LED of various spectrum as well as full spectrum preferred in our invention.

FIG. 2C(I) the LED element with its necessary optic was arranged in a matrix, the 10B1-10B9 fine individual light element was arranged to shine on the corresponding area of B1-B9 respectively above cornea. The other light source element 10L need not so delicate was arranged to shine on area of A1, A2, A3 with its necessary customized optic adhere to guide its light direction. 40A is a infra-red light source shine on cornea and 40B is a camera for pupil detector. The pupil detector is well known technology for decades.

FIG. 2C(II) is an option of 10B1-10B9, be arranged in a horizontal version, pupil detector 40A and 40B be arranged in a more separate version and merged with light source element 10L.

Figures 3, 4, 5, 7:
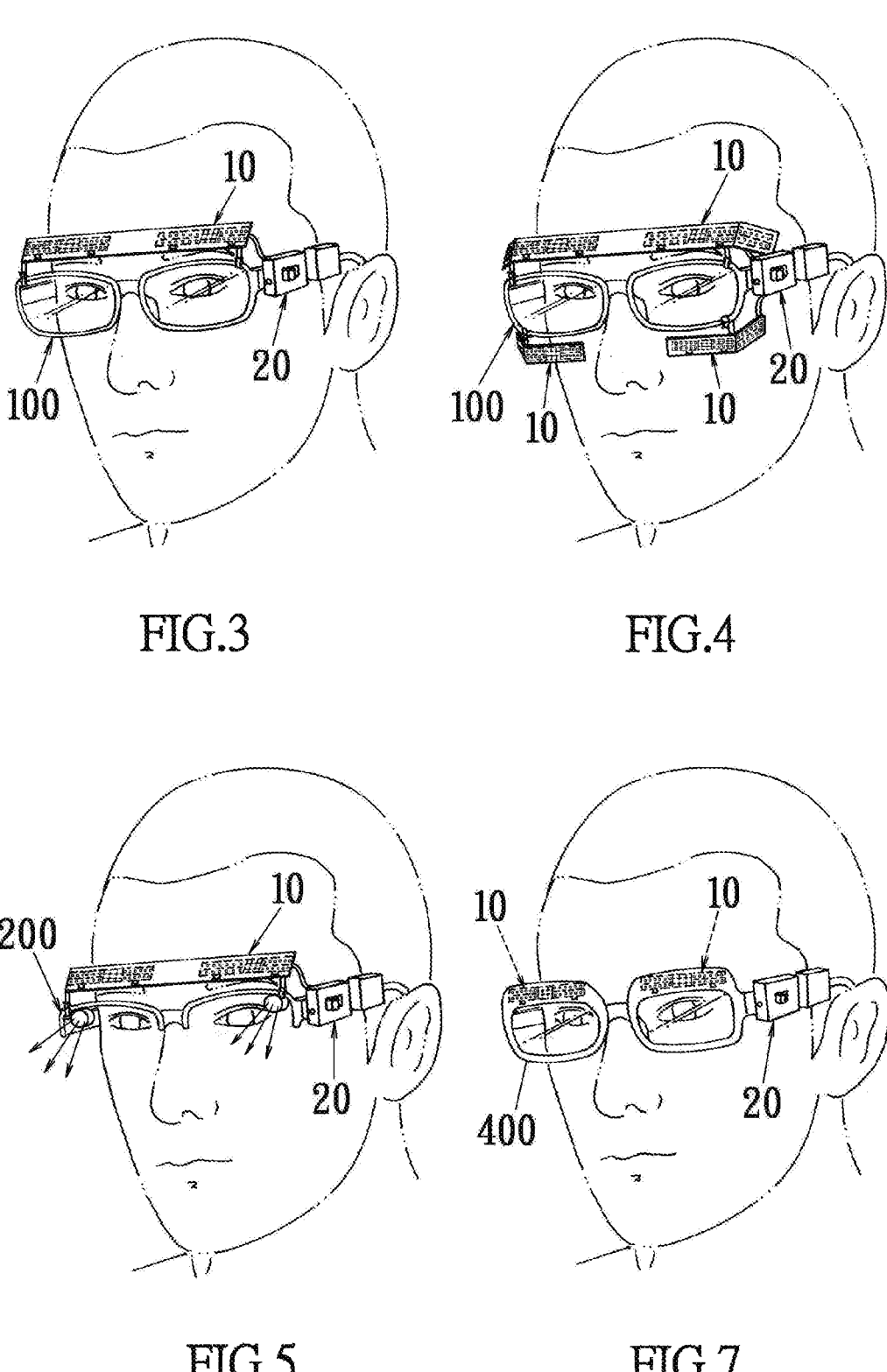
FIG. 3 is the schematic diagram of the 1$^{st}$ embodiment of the present invention.
FIG. 4 is the schematic diagram of the 2$^{nd}$ embodiment of the present invention.
FIG. 5 is the schematic diagram of the 3$^{rd}$ embodiment of the present invention.
FIG. 7 is the schematic diagram of the 5$^{th}$ embodiment of the present invention.

FIG. 3 is the 1$^{st}$ embodiment of the present invention, A light source 10 is provided above an existing pair of glasses 100, and the light source 10 can be clamped and fixed on the pair of glasses 100 by using a clamp, while a CPU controller 20 is clamped and fixed next to the light source 10 and electrically connected to the light source 10. Light source 10 comprises fine light elements (10B1-10B9) to shine on peripheral cornea area were merged in frame of light source 10 was regulated by pupil detector to avoid high intensity light shine into pupil.

FIG. 4 is the 2$^{nd}$ embodiment of the present invention, at least one light source 10 is clamped and fixed above, below, or laterally to an existing pair of glasses 100, while at least one CPU controller 20 is clamped and fixed next to the light sources 10 and electrically connected to the light sources 10. Light source 10 comprises fine light element to shine on cornea area was regulated by pupil detector which merged in frame of light source 10 to avoid high intensity light shine into pupil.

FIG. 5 is the 3$^{rd}$ embodiment of the present invention, A person wears an illumination device frame 200, wherein the illumination device frame 200 is provided thereon with at least one light source 10, while a CPU controller 20 is provided next to the light source 10 and electrically connected to the light source 10; Illumination provided by the light source 10 can be individually controlled, or collectively controlled by a unit related to a main program of the illumination device frame 200. Light source 10 comprises fine individual light elements to shine on cornea area was regulated by pupil detector which merged in frame of light source 10 to avoid high intensity light shine into pupil.

Figure 6:
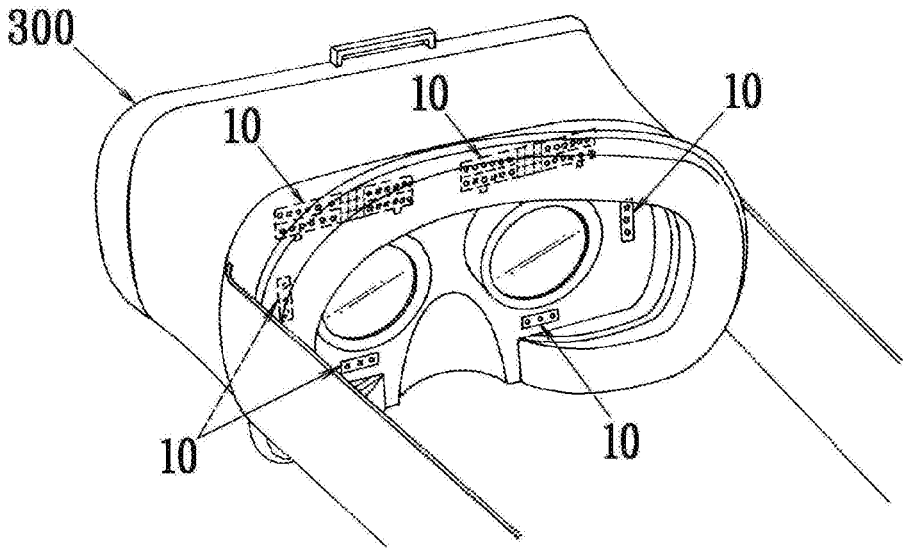
FIG. 6 is the schematic diagram of the 4$^{th}$ embodiment of the present invention.

FIG. 6 is the 4$^{th}$ embodiment of the present invention, A pair of virtual reality (VR) or augmented reality (AR) set 300, wherein the pair of VR or AR set 300 or a frame similar thereto such as other head mount display is provided thereon with at a light source 10, while a CPU controller 20 is provided next to the light source 10 and electrically connected to the light source 10; illumination provided by the light source 10 can be individually controlled, or collectively controlled by a unit related to a main program of the pair of VR or AR set 300 or the frame similar thereto. Light source 10 comprises fine individual light elements to shine on peripheral cornea area was regulated by pupil detector which merged in frame of light source to avoid high intensity light shine into pupil.

FIG. 7 is the 5$^{th}$ embodiment of the present invention, It comprising a customized glasses frame 400, at least one light source 10 is directly provided on the glasses frame 400 so as to provide illumination, while a CPU controller 20 is provided next to the light source 10 and electrically connected to the light source 10. Light source 10 comprises fine individual light elements to shine on peripheral cornea area was regulated by pupil detector which merged in frame of light source 10 to avoid high intensity light shine into pupil.

Figure 8:
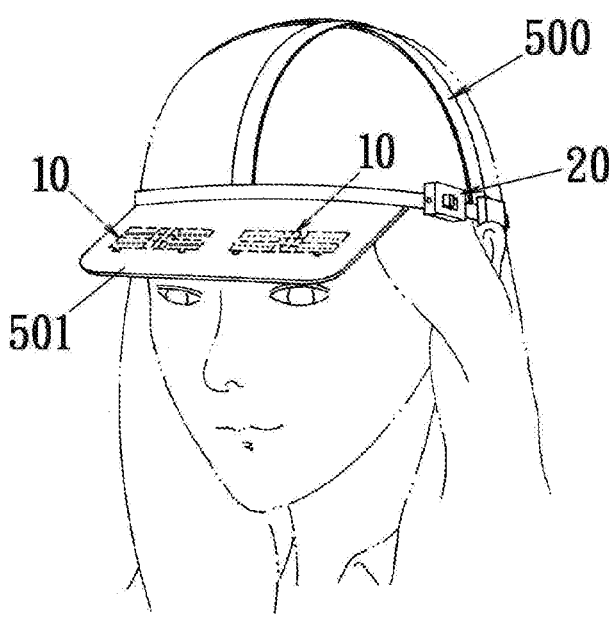
FIG. 8 is the schematic diagram of the 6$^{th}$ embodiment of the present invention.

FIG. 8 is the 6$^{th}$ embodiment of the present invention, It comprising a customized headgear 500, and at least one light source 10 is provided on an edge 501 of the headgear 500, while a CPU controller 20 is provided in an adequate position on the headgear 500, and the CPU controller 20 is electrically connected to the light source 10. Light source 10 comprises fine individual light elements to shine on peripheral cornea area was regulated by pupil detector which merged in frame of light source 10 to avoid high intensity light shine into pupil.

In summary, the present invention is to construct a device which mimic the outdoor high illumination in real life, the high intensity light of outdoor activity can prevent myopia progression, protect human heart, prevent DM, healthy for human, all have proved by strict study, but the averaged light intensity of sunny daylight is 40000 to 120000 lux and up excess to 200000, which definitely cannot be allowed to pass directly through pupil into eyeball, the majority of daylight shine mostly on periorbital skin and enter eyeball through an extra pupillary pathway. Our invention is to fulfill the high intensity light illumination of outdoor activity and improve the efficiency by wearable, direct extra pupillary illumination, with improved duty time control, intensity control, which will be helpful for people lack outdoor time.

It is of course to be understood that the embodiments described herein are merely illustrative of the principles of the invention and that a wide variety of modifications thereto may be effected by persons skilled in the art without departing from the spirit and scope of the invention as set forth in the following claims.

REFERENCE

1. What Do Animal Studies Tell Us about the Mechanism of Myopia-Protection by Light?
Norton T T. Optom Vis Sci. 2016 September; 93(9):1049-51. doi: 10.1097/OPX.0000000000000917.
2. Animal Studies and the Mechanism of Myopia-Protection by Light?
Ashby R. Optom Vis Sci. 2016 September; 93(9):1052-4. doi: 10.1097/OPX.0000000000000978.
3. The effect of bright light on lens compensation in chicks.
Ashby R S, Schaeffel F. Invest Ophthalmol Vis Sci. 2010 October; 51(10):5247-53. doi: 10.1167/iovs.09-4689. Epub 2010 May 5.
4. Correlation between light levels and the development of deprivation myopia.
Karouta C, Ashby R S. Invest Ophthalmol Vis Sci. 2014 Dec. 9; 56(1):299-309. doi: 10.1167/iovs.14-15499.
5. The effect of ambient illuminance on the development of deprivation myopia in chicks.
Ashby R, Ohlendorf A, Schaeffel F. Invest Ophthalmol Vis Sci. 2009 November; 50(11):5348-54. doi: 10.1167/iovs.09-3419. Epub 2009 Jun. 10.
6. Light levels, refractive development, and myopia—a speculative review.
Norton T T, Siegwart J T Jr. Exp Eye Res. 2013 September; 114:48-57. doi: 10.1016/j.exer.2013.05.004. Epub 2013 May 13.
7. Protective effects of high ambient lighting on the development of form-deprivation myopia in rhesus monkeys.
Smith E L 3rd, Hung L F, Huang J. Invest Ophthalmol Vis Sci. 2012 Jan. 25; 53(1):421-8. doi: 10.1167/iovs. 11-8652.
8. Influence of periodic vs continuous daily bright light exposure on development of experimental myopia in the chick.
Backhouse S, Collins A V, Phillips J R. Ophthalmic Physiol Opt. 2013 September; 33(5):563-72. doi: 10.1111/opo.12069. Epub 2013 May 13.
9. Bright Light Suppresses Form-Deprivation Myopia Development With Activation of Dopamine D1 Receptor Signaling in the ON Pathway in Retina.
Chen S, Zhi Z, Ruan Q, Liu Q, Li F, Wan F, Reinach P S, Chen J, Qu J, Zhou X. Invest Ophthalmol Vis Sci. 2017 Apr. 1; 58(4):2306-2316. doi: 10.1167/iovs.16-20402.
10. Intense Light-Mediated Circadian Cardioprotection via Transcriptional Reprogramming of the Endothelium Oyama et al., (2019, Cell Reports 28, 1471-1484)
11. Rev Physiol Biochem Pharmacol 2012; 162:59-90.doi: 10.1007/112_2011_4. Intrinsically photosensitive retinal ganglion cells Gary E Pickard 1, Patricia J Sollars

What is claimed is:

1. A myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, comprising multiple light sources, two units for pupil detector and a CPU controller and a battery pack for system power supply, the two units for pupil detector detect a size of a pupil;

wherein the pupil detector sends a photo of a position of the pupil to the CPU controller, the CPU controller calculates whether the position of the pupil overlaps with an illuminating position of fine individual light element of light source, when any of the fine individual light element illuminates an area overlap with a pupil region, the CPU controller makes a calculation and shuts off the fine individual light element to prevent high intensity light from entering into the pupil.

2. The myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, according to claim 1, wherein the light illuminating cornea region is controlled by two units for pupil detector and the CPU controller to avoid high intensity light to pass through pupil aperture.

3. The myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, according to claim 1, wherein each light source of the multiple light sources comprises various spectra, wherein the spectra and compositions thereof can be adjusted according to a requirement, the light source is one type of light source or a composition of various light sources, the illumination level provided by the light source is adjustable, and being adjusted to greater than 0.5 LUX or program adjusted based on different time periods; the illumination timing of the illumination provided by the light source being continuous, intermittent, or adjusted by preset program.

4. The myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, according to claim 1, the light illuminating eyeballs and surrounding tissue through an extra-pupillary pathway.

5. The myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, according to claim 1, the light intensity of each light source of the multiple light sources is in a range extending from 1000 lux to 120000 lux.

6. The myopia-preventing high intensity illumination apparatus for illuminating eyeballs and surrounding tissues by extra pupillary pathway via light that penetrating periorbital skin, subcutaneous tissue, pass through peripheral cornea, iris, peripheral lens, uvea, sclera, choroid, retinal pigment epithelium, according to claim 1, wherein a light spectrum is full spectrum of sunny daylight.

7. The myopia-preventing high intensity illumination apparatus for illuminating eyeballs and surrounding tissues by extra pupillary pathway via light that penetrating peri-orbital skin, subcutaneous tissue, pass through peripheral cornea, iris, peripheral lens, uvea, sclera, choroid, retinal pigment epithelium, according to claim 1, wherein each light source of the multiple light sources is provided above, below or laterally to a pair of glasses.

8. The myopia-preventing high intensity illumination apparatus for illuminating eyeballs and surrounding tissues by extra pupillary pathway via light that penetrating peri-orbital skin, subcutaneous tissue, pass through peripheral cornea, iris, peripheral lens, uvea, sclera, choroid, retinal pigment epithelium, according to claim 1, wherein the light source and necessary components being provided on a pair of VR or AR set or a frame similar thereto, wherein illumination provided by each light source of the multiple light sources being individually controlled, or collectively controlled by a main program of the pair of VR or AR set or the frame similar thereto.

9. The myopia-preventing high intensity illumination apparatus for illuminating eyeballs and surrounding tissues by extra pupillary pathway via light that penetrating peri-orbital skin, subcutaneous tissue, pass through peripheral cornea, iris, peripheral lens, uvea, sclera, choroid, retinal pigment epithelium, according to claim 1, wherein each light source of the multiple light sources and necessary components being constructed to merge with a glasses frame.

10. The myopia-preventing high intensity illumination apparatus for illuminating eyeballs and surrounding tissues by extra pupillary pathway via light that penetrating peri-orbital skin, subcutaneous tissue, pass through peripheral cornea, iris, peripheral lens, uvea, sclera, choroid, retinal pigment epithelium, according to claim 1, wherein each light source of the multiple light sources and necessary components being constructed to merge with an illumination device frame.

11. The myopia-preventing high intensity illumination apparatus for illuminating eyeballs and surrounding tissues by extra pupillary pathway via light that penetrating peri-orbital skin, subcutaneous tissue, pass through peripheral cornea, iris, peripheral lens, uvea, sclera, choroid, retinal pigment epithelium, according to claim 1, wherein each light source of the multiple light sources and necessary components being constructed to merge with a headgear.

* * * * *